United States Patent [19]

Christensen et al.

[11] Patent Number: 4,784,860

[45] Date of Patent: Nov. 15, 1988

[54] PET FOOD

[75] Inventors: Flemming M. Christensen, Copenhagen; Hans A. S. Olsen, Holte, both of Denmark; Columbus O. L. Boyce, Brewster, N.Y.

[73] Assignee: Novo Industri A/S, Bagsvaerd, Denmark

[21] Appl. No.: 921,414

[22] Filed: Oct. 22, 1986

[30] Foreign Application Priority Data

Nov. 4, 1985 [DK] Denmark .............................. 5063/85

[51] Int. Cl.$^4$ ............................................... C23K 1/00
[52] U.S. Cl. ........................................ 426/46; 426/53; 426/54; 426/630; 426/805
[58] Field of Search ...................... 426/54, 46, 49, 52, 426/53, 60, 623, 630, 805, 656

[56] References Cited

U.S. PATENT DOCUMENTS

| | | | |
|---|---|---|---|
| 3,640,723 | 2/1972 | Unlig et al. | 426/656 |
| 4,391,829 | 7/1983 | Spradlin et al. | 426/623 |
| 4,393,085 | 7/1983 | Spradlin et al. | 426/646 |
| 4,478,939 | 10/1984 | Adler-Nissen | 426/49 |
| 4,483,874 | 11/1984 | Olsen | 426/44 |

Primary Examiner—R. B. Penland
Attorney, Agent, or Firm—Morris Fidelman; Franklin D. Wolffe

[57] ABSTRACT

A pet food containing a proteinaceous vegetable source component treated with an SPS-ase preparation in aqueous medium. Presence of this component imparts a decisive improvement in regard to the elasticity and palatability of the pet food.

3 Claims, No Drawings

PET FOOD

This invention relates to pet foods of improved palatability and texture.

INTRODUCTION

The art relating to pet food is huge. Just to mention a few examples, reference is made to patent application No. PCT/US 82/01198; BE Pat. No. 856,265; G.B. Pat. No. 2,041,717; and U.S. Pat. Nos. 4,190,679; 4,393,085; 4,055,676, 3,959,511; 3,202,514; 3,617,300; 3,857,968; 4,158,706 and 4,391,829.

For the purpose of this invention, it is intended that the term pet food should be understood to mean a nutritionally adequate food composition prepared for mammals, and notably for dogs and/or cats, and also that the pet foods are classified into the dry type, the soft-dry type, the semi-moist type and the canned type.

Dry pet foods are crunchy products with major components variously of corn, wheat, soybean oil meal, meat/bone meal and tallow. The dry pet food products are among the least palatable for the pets. In order to increase palatability, the product may be coated with an enzymatically treated fat and protein mixture, for instance as suggested by U.S. Pat. No. 3,857,968.

A more chewy and palatable product is the soft-dry product type that contains meat or meat by-products. Besides ingredients already mentioned, the soft-dry pet food often contains propylene glycol and glycerol. Propylene glycol is used for preservation purposes and glycerol is used as a plasticizer in order to create an extruder product of desirably chewy and meat-like texture.

The dry and soft-dry product types are most often made by blending the dry components (e.g., corn, wheat, soybean meal, meat/bone meal, vitamin/mineral mix) and extruding the blend with added steam, water and where used, propylene glycol/glycerol. Both single and twin screw extruders are used. After drying, the extruded pellets may be coated with fat or a gravy for palatability improvement purposes. Typically, dry pet foods have moisture content of less than 12% w/w while soft-dry pet foods have moisture content of 18–25% w/w.

The semi-moist product types constitute a more expensive product category, offering the mammal pet a more meat-like product with better appearance and palatability. In semi-moist pet food processing, a cooked slurry of meat, meat by-products, corn syrup, water and propylene glycol is mixed and cooked with soy grits, soybean meal and vitamin/mineral mix, before being extruded and formed into noodles or chunks. Semi-moist products usually have a moisture content of 25–30% w/w.

The most palatable and most expensive pet food product category is the canned product. The main ingredients are meat and meat by-products along with TVP (textured vegetable protein) chunks, soy grits and vitamin/mineral mix, and, of course, water. Moisture content is usually 75–80% w/w.

The present invention is directed toward improving the palatability of pet foods. Additionally, the texture of dry, soft-dry, semi-moist and canned pet foods is improved. The term "texture: is intended to indicate the extent to which the pet food constitutes a meat-like product. One of the chief attributes of good texture is chewiness or resistance to bite without shattering. The hardness and elasticity measurements employed herein correlate to chewiness and, therefore, to texture.

BACKGROUND OF THE INVENTION

The palatability of pet food may be improved by an enzymatic pre-treatment of the ingredients. Reference is made to U.S Pat. No. 3,857,968 which suggests a lipase and protease treatment of fat and protein containing ingredients improving palatability, and to U.S. Pat. Nos. 4,391,829 and 4,393,085, which suggest an amylase and a protease pre-treatment of farinaceous and proteinaceous ingredients of an extruded pet food to improve the palatability thereof. Although such treatments may be employed along with practice of this invention, if desired, the discussion which follows ignores this possibility.

It is noted that research efforts toward achieving best nutritional value, improve palatability and meat-like feel in all pet food types, are within severe product cost constraints. Above all, the pet food product must remain relatively inexpensive. Appropriately enough, all pet foods contain some protein of vegetable origin, e.g., soy, corn, etc., such being a relatively inexpensive form of protein. Reference can be made to e.g., U.S. Pat. No. 3,202,514, Example 1, wherein it is indicated that 36.5% of the pet food consists of soy flakes.

Now surprisingly, according to the invention, it has been found that pet foods can be improved considerably in regard to platability and texture if the vegetable protein material component therein has been exposed to an enzymatic modification, viz a treatment with an SPS-ase preparation in aqueous medium.

BRIEF STATEMENT OF THE INVENTION

Thus, the pet food, according to the invention, comprises as a component a proteinaceous material which is a vegetable protein modified by treatment with an SPS-ase preparation in an aqueous medium. The modified vegetable protein should be at least 10% w/w dry substance basis of the pet food.

Surprisingly, it has been found that the pet food, according to the invention, has a better palatability and texture than conventional pet foods. Also surprisingly, it has been found that the need for inclusion of propylene glycol in soft-dry pet foods is reduced substantially, hopefully eliminated altogether. It is believed that this result is related to the fact that the pet food composition of this invention has an increased soluble saccharide content due to the action of the SPS-ase on the vegetable protein source. The reason for incorporating propylene glycol is to provide humectancy and/or to inhibit microorganism growth. The soluble saccharides generated from the vegetable protein source generate humectancy results.

DISCUSSION OF THE INVENTION

For the purpose of this Specification, it is intended that the term proteinaceous vegetable material is understood to comprise any proteinaceous plant derived material suited for pet food, e.g., whole ground corn (maize), whole ground wheat, whole ground faba beans, whole ground peas, any soy based material, whole ground rape, whole ground barley, whole ground rye, etc.

Also, for the purpose of this Specification, it is intended that the term SPS-ase preparation is understood to mean a preparation of SPS-ase as described and defined in U.S. Pat. No. 4,478,939. Only SPS-ase is contemplated for practice of this invention. A similar texture improving effect does not appear if a similar treatment is carried out with proteinase, e.g., ALCALASE TM or a mixture of pectinase; e.g., PECTINEX TM and cellulase; e.g., CELLUCLAST TM and thus, it is assumed that a principal active principle pertaining to the treatment of the proteinaceous material with an SPS-ase preparation is the SPS-ase enzyme itself.

Also, for the purpose of this Specification, it is intended that the term "the proteinaceous material is treated with an SPS-ase preparation in an aqueous medium" is understood to mean that the proteinaceous material and the SPS-ase preparation are brought together at such pH, temperature and enzyme concentration in an aqueous medium that substantial enzymatic action takes place. Preferably, the enzymatic process is carried out to completion, e.g., by treatment of 100 g of proteinaceous material which, for example, may be jet-cooked soy meal, slurried with 400–800 ml of water with an SPS-ase preparation of SPS-ase activity between 20 and 200 SPSU/g (as defined in AF 201/1-GB-a, available on request from NOVO INDUSTRI A/S, Novo Alle, 2880 Bagsvaerd, Denmark) at a pH of 4–6.5 and a temperature of 40°–55° C. for 4–24 hours Thus, this above process may follow the practice described in U.S. Pat. No. 4,483,874 for the process for treatment of the vegetable protein.

In a preferred embodiment of the pet food, according to the invention, the proteinaceous material of vegetable origin is a soy based material, more preferably is soy meal. Soy based materials are cheap and are frequently used as a component in pet food. For the purpose of this Specification, it is intended that the term "soy based material" is understood to mean a commercial form of soy protein, e.g., whole soy beans, soybean meal, soy flakes, or soy concentrate. However, soybean meal constitutes the preferred soy based material, according to the invention, inasmuch as soybean meal is economical and is well suited both for treatment with the SPS-ase preparation and for incorporation into the pet food as a constituent. To repeat, the treated vegetable protein material should comprise at least about 10% w/w dsb of the pet food.

In a preferred embodiment of the pet food, according to the invention, the SPS-ase preparation is producible by means of *Aspergillus aculeatus* CBS 101.43. In this way, a fully satisfactory SPS-ase preparation is provided and with its use on the vegetable protein, a pet food with fully satisfactory palatability and texture results.

In a preferred embodiment of the pet food, according to the invention, the enzymatic treatment of the vegetable protein is carried out to completion or substantially to completion. In this manner, a pet food with fully satisfactory palatability and texture is provided.

The action of SPS-ase is principally on the non-protein constituents of the vegetable protein material. Soy meal, a common vegetable protein material in pet food formulations is a defatted product (e.g., less than 1% fat w/w) rich in protein, containing, for example, 44–52% w/w of protein (dry substance basis). Aside from some ash, the remaining ingredients in the soy meal are non-starch polysaccharides largely, if not entirely, indigestible by monogastric animals, e.g., dogs, cats, pigs. It is believed that the polysaccharides are non-functional, even non-beneficial to the texture of soft-dry and semi-moist pet foods. It is likely, that the enzymatic action of the SPS-ase improves digestibility of the polysaccharide component. However, palatability of the ultimate pet food is improved.

A demonstrable benefit of the enzymatic action of SPS-ase is to transform the largely, if not entirely (non-functional), polysaccharide component into a texture improving ingredient. Use of SPS-ase modified soy meal allows a pet food manufacturer to produce a pet food product at a moisture level of 18% with the same softness as a product containing 25% water and propylene glycol (which functions as a humectant and an anti-microbial agent). In addition, the product containing enzyme-treated soy meal has more elasticity and, therefore, more chewiness than the higher moisture product. Need for propylene glycol for humectant purposes is avoided. (Some propylene glycol may still be desirable for anti-microbial purposes.)

One instance wherein reduction in water content achievable by use of SPS-ase treated soy meal is particularly advantageous constitutes dual-texture pet foods. Such products are a blend of dry, crunchy nuggets and chewy, soft-dry (or soft-moist) pieces. Because the chewy pieces contain about 25% moisture w/w and the dry nuggets 8–12% w/w moisture, a moisture imbalance exists within the packaged dual texture product. Moisture migration takes place, causing the chewy pieces to become hard and the dry nuggets to lose their crunchy character. The lower moisture content of chewy pieces formulated with SPS-ase treated soy meal reduces the moisture content differential between the dry nuggets and the chewy pieces, thereby reducing the moisture migration rate to provide a longer shelf life for the dual texture product.

On the whole, the formulator of a soft-dry or semi-moisture pet food is offered more freedom of choice than heretofore toward formulation of a pet food with a particular level of elasticity, softness, frangibility, etc., the measurable characteristics of good texture. Employment of the SPS-ase treated vegetable protein allows reduction in either or both the propylene glycol content and the water content. Desirably, use of SPS-ase treated vegetable protein allows for a soft-dry pet food with near to the 18% w/w moisture content lower limit for the soft-dry category of pet foods.

Use of SPS-ase treated vegetable protein on dry pet foods is also advantageous. Palatability is improved. The humectant attribute generated in the polysaccharide moiety by the enzyme treatment of the vegetable protein need not destroy the crunchy characteristic.

The pet food, according to the invention, can be produced by extrusion, as has already been indicated, but several other methods may be used as well, provided that the starch component of the pet food is gelatinized in admixture with the SPS-ase treated proteinaceous material.

According to the invention, the pet food will be illustrated by the following Examples.

EXAMPLE 1

Five pet foods, I–V with the following compositions were provided:
Pet food I:
 50% wheat meal ("Unika" from Valsemollen, Postbox 142, 6701 Esbjerg, Denmark)
 25% bone meal (from DLG, Axelborg, Vesterbrogade 44, 1503 Copenhagen V, Denmark)
 25% soy meal (Soyamel 13 from Aarhus Oliefabrik, M. P. Bruunsgade 27, Postbox 50, 8100 Arhus C).

Pet food II:
Like I, but the last component was jet-cooked soy meal. The jet-cooked soy meal was prepared in the following manner:
79.9 kg of defatted soy meal (Sojamel 13 from Aarhus Oliefabrik A/S) was mixed with 295 l of water. The slurry was jet-cooked at 150° C. for 30 seconds and subsequently spray-dried.

Pet food III:
Like I, but the last component was SPS-ase treated soy meal. The SPS-ase treated soy meal was made as follows:
75 kg of defatted soy meal (Sojamel 13 from Aarhus Oliefabrik A/S) was mixed with 285 l of water. The slurry was jet-cooked at 150° C. for 30 seconds. pH was adjusted to 4.5 by addition of 2200 ml of 12N HCl. SPS-ase treatment was carried out for 24 hours at 45° C. by addition of 1407 g of the SPS-ase containing enzyme preparation SP-249 PPS 1540, as described in NOVO ENZYME INFORMATION IB-297b-GB. After hydrolysis the SPS-ase preparation was inactivated by heating the slurry to 85° C. for 2 minutes, and subsequently the slurry was spray-dried.

Pet food IV:
Like I, but the last component was protease treated soy meal. The protease treated soy meal was prepared as follows:
33.3 kg of defatted soy meal (SojAmel 13 from Aarhus Oliefabrik A/S) was mixed with 186 l of water. Protease treatment was carried out at 55° C. and pH=8 by addition of 351 g of the alkaline protease Alcalase 0.6 L, as described in NOVO INFORMATION LEAFLET B-207c-GB. Hydrolysis was carried on until a degree of hydrolysis of 3% was reached, as described in NOVO INFORMATION LEAFLET B-163f-GB. After hydrolysis the enzyme was inactivated by lowering the pH to 4.0 for 30 min., and subsequently the slurry was spray-dried.

Pet food V:
Like IV, but the double amount of Alcalase 0.6 L was used, and the hydrolysis was carried on to a degree of hydrolysis of 10%.

The formulations I—V were cooked and extruded on a Werner & Pfleiderer Continua C 37 twin screw extruder with an L/D proportion of 22 (L/D=length of screw/diameter of screw) corresponding to a holding time in the extruder of 0.75 minutes to 1 minute.

The dry formulations were fed to the extruder with a rate of 35 kg/h. Directly after the feed funnel water was added with a rate of 6.0–6.5 kg/h by means of a piston pump. The water contained 2.5% w/w of potassium sorbate. The temperature in the screw houses Nos. 2–5 were kept constant at 150° C., whereas screw house No. 1 was cooled. The extrudate was pressed through two cylindrical nozzles with a diameter of 6 mm each. The rotational speed of the screws was 300 rpm. Directly downstream the exit nozzle of the extruder the extrudate was cut into small pellets by means of a rotating knife.

The elasticity was measured by means of an Instron apparatus. The sample to be tested is placed below a flat pressure plate in the Instron apparatus. With a velocity of 20 mm/minute the pressure plate is directed towards the sample, which is compressed to ⅓ of the original sample height. The force required for the compression is recorded as a function of the compression (as a "working curve") with a coupled writing recorder with a paper velocity of 200 mm/minute. Five consecutive compressions were performed. The elasticity in % is defined as the proportion between the area below the 5' and 1' working curve i.e.

$$\text{elasticity} = \frac{A_5}{A_1} \times 100\%$$

The data from the elasticity test can be used for the hardness determination, as the hardness is the initial gradient on the 1' working curve. Thus, the hardness is the hardness of the not deformed sample, expressed as pressure per length unit of compression, e.g. in N/mm³.

The samples I, II, IV, and V showed no remarkable difference in regard to elasticity and softness, whereas the SPS-ase treated sample III had a much softer and much more elastic texture.

Comparative Instron-measurements were made on samples of I and III. The samples were also analyzed for percentage of dry matter.

The results were:
Pet food I: % of dry matter=82.0%
Pet food III: % of dry matter=83.0% and

|  | Elasticity (%) | Hardness (N/mm³) |
|---|---|---|
| Pet food I |  |  |
| Sample A | 18.1 | 0.508 |
| Sample B | 17.2 | 0.469 |
| Sample C | 15.5 | 0.547 |
| Sample D | 16.4 | 0.664 |
| Pet food III |  |  |
| Sample A | 28.0 | 0.234 |
| Sample B | 26.0 | 0.372 |
| Sample C | 24.6 | 0.216 |
| Sample D | 29.1 | 0.273 |
|  | Average elasticity ± s.d. | Average hardness ± s.d. |
| Pet food I (−SPS-ase treatment) | 16.8 ± 1.1% | 0.547 ± 0.084 N/mm |
| Pet food III (+SPS-ase treatment) | 26.9 ± 2.0% | 0.274 ± 0.070 N/mm |

Thus, by treating the soy based fraction of a pet food with an SPS-ase, a pet food with improved elasticity and greater softness may be obtained.

EXAMPLE 2

Two pet foods, A and B, were tested, A being a pet food according to the invention, and B being a corresponding prior art pet food control.

Composition of A:
50% wheat meal ("Unika" from Valsemollen)
25% meat bone meal (from DLG)
25% jet-cooked soy meal, treated with SPS-ase The jet-cooked soy meal treated with SPS-ase, was prepared in the following manner.

33 kg of defatted soy meal (ground "White Flakes 09" from Aarhus Oliefabrik A/S) was mixed with 222 l of water. The slurry was jet-cooked at 150° C. for 25 seconds. pH was adjusted to 4.52 by addition of 1350 ml 12N HCl. SPS-ase-treatment was carried out for 24 hours at 45° C. by addition of 638 g of the SPS-ase-containing enzyme preparation SP 249 PPS 1612, as described in NOVO ENZYME INFORMATION IB 297c-GB. This enzyme preparation has an SPS-ase-activity of 30 SPSU/g. After hydrolysis the temperature of the slurry was raised to 85° C. for 2 minutes in order to inactivate the SPS-ase-preparation. Finally the slurry was spray-dried.

The SPS-ase-treated soy meal was mixed with wheat meal and meat-bone meal according to the above proportions. The dry mixture was extruded as described previously, with the following exceptions: the rate was 50 kg/h, water was added at a rate of 9.5–10.0 kg/h, and the extrudate was pressed through one cylindrical nozzle with a diameter of 7 mm.

The extruded pet food A exhibited the following characteristics:
% protein (N×6.25)=33.0% (based on dry matter)
% dry matter=80.3%
Composition of B:
Like A, but last component was 25% plain defatted soy meal.

The extruded pet food B exhibited the following characteristics:
% protein (N×6.25)=31.8% (based on dry substance)
% dry matter=79.9%.

By means of the Instron Apparatus it was shown that A had a 17% higher elasticity and a 17% lower hardness than B.

Furthermore, dog feeding experiments were carried out with pet foods A and B. Five dogs (Nos. 447, 467, 476, 481, and 486) were fed with pet foods A and B for two days. Each forenoon each of the five dogs were offered 2 batches of 320 g each, one batch of pet food A, and one batch of pet food B. The two batches were served simultaneously, allowing the dogs a free choice between the two batches. It was found that each dog first was sniffing to both batches, whereafter they started to eat batch A. None of the dogs started to eat batch B, before they had finished batch A. Two dogs (Nos. 481 and 486) ate up both batches within 15 minutes. Late in the afternoon the rest of the dogs had eaten up the entire amount of batch a, but hardly touched batch B. The next norming the remainder of batch B had been eaten as well.

Samples of A and B were stored at ambient temperature (20°–25° C.) for 9 months. Subsequently, both samples were inspected. Sample B (without SPS-ase treatment) had turned green/grey, was covered with mold and had an unpleasant odour. Sample A (with SPS-ase treatment) showed no sign of microbial deterioration and appeared as when extruded 9 months earlier. None of the samples A and B contained propylene glycol.

EXAMPLE 3

As in example 2, two pet foods, A and B, were tested, A being a pet food according to the invention, and B being a corresponding prior art pet food control. The compositions of A and B in this example differed slightly from the composition of A and B in exmple 2, as shown below:
A in this example:
40% whole ground corn,
20% whole ground wheat,
20% meat- and bone-meal,
20% jet-cooked soy flour, treated with SPS-ase.
B in this example:
40% whole ground corn,
20% whole ground wheat,
20% meat- and bone-meal,
20% soy flour.

Otherwise the preparation of the two pet foods, including the SPS-ase treatment and the extrusion, were carried out exactly as indicated in example 2. The elasticity test was carried out as in example 2, with the following exceptions: (1) the velocity of the pressure plate was 100 mm/minute (2) the paper velocity was 1000 mm/minute, and (3) the samples were compressed to ½ of the original sample height.

Feeding trials comprising 20 dogs of various breeds and sizes were conducted at a kennel. A table of the participating dogs is shown in Table 2.

12 dogs were fed for 14 days, 4 dogs for 11 days, 2 dogs for 7 days and 2 dogs for 4 days with the A and B pellets.

Each day the dogs were offered simultaneously 2 bowls with A and B, respectively. Each portion was of the order of 25 g pellets/kg body weight. Thus a small dog of 10 kg was simultaneously offered 250 g A and 250 g B, while a big dog of 50 kg was offered 1250 g A and 1250 g B. The dog was allowed to eat for 45 minutes, after which time the bowls were removed, and the remaining amount of pellets were weighed.

For every day of feeding the position of the bowls was reversed in order that the dogs would have to make a deliberate choice, as to which feed it preferred.

To ease the interpretation of the results the preference percentages for A and B, respectively, are defined as $$pA = \frac{EA}{EA + EB} \times 100\%$$

$$pB = \frac{EB}{EA + EB} \times 100\% \; (\approx 100 - pA)$$

EA=daily consumption of A
EB=daily consumption of B
Results

The dry substance (H) and protein (P) analysis gave the following results:

|  | H % | P % (N × 6.25) | $\frac{P \% \times 100}{H \%}$ |
| --- | --- | --- | --- |
| Dry mixed powder A | 89.0 | 24.7 | 27.8 |
| Dry mixed powder B | 89.1 | 24.5 | 27.5 |
| Pellets A | 82.0 | 23.2 | 28.3 |
| Pellets B | 83.2 | 23.1 | 27.8 |

The elasticity and hardness data are given in Table 1, and the results of the big feeding trial is outlined in Table 2.
Discussion The elasticity and hardness data for the pellets A and B are compared to data for a commercially available soft-dry product, vide Table 1.

In order to simplify the numerous data in Table 1, the average elasticity and hardness data are calculated:

| Pet Food | Average elasticity % | Standard deviation % | Confidence interval 95% level |
| --- | --- | --- | --- |
| A | 26.1 | 5.0 | 26.1 ± 3.6 |
| B | 13.0 | 8.2 | 13.0 ± 5.9 |
| Commercial Product | 9.4 | 3.2 | 9.4 ± 2.5 |

| Pet food | Average hardness N/mm$^3$ | Standard deviation N/mm$^3$ | Confidence interval 95% level |
| --- | --- | --- | --- |
| A | 0.58 | 0.29 | 0.58 ± 0.21 |

| | -continued | | |
|---|---|---|---|
| B | 2.55 | 1.33 | 2.55 ± 0.95 |
| Commercial Product | 0.31 | 0.15 | 0.31 ± 0.12 |

With regard to elasticity the A product is much superior both to the reference product B and to the commercial product.

The low elasticity score for the commercial product is due to the fact, that these pellets break when being pressed together.

There is no statistically significant difference between the elasticity of B and the commercial product.

When looking at the hardness data, big differences are seen, too. The A product and the commercial product are much softer than B. However, the soft texture of the A product is due to the SPS-ase treatment of the soy flour ingredient, while commercial products are soft due to the presence of propylene glycol, and high moisture content (of about 25% w/w).

Therefore, SPS-ase treatment gives rise to a pet food, which is soft and elastic, while propylene glycol and higher moisture content generates softness, but only little elasticity of the pet food.

The results of the feeding trial may briefly be summarized as follows:

| | 95% level | 99% level |
|---|---|---|
| Number of dogs with preference for A | 14 | 9 |
| Number of dogs with preference for neither A nor B | 5 | 10 |
| Number of dogs with preference for B | 1 | 1 |

Another way of arranging the data of Table 2 is to calculate the total consumption of A and B during the trial. Put in this way, the result is:

| | A | B |
|---|---|---|
| Total amount of feed offered, kg | 143.125 | 143.125 |
| Total amount of feed eaten, kg | 82.150 | 40.150 |
| Overall preference, % | 67.2 | 32.8 |

From both sets of data it appears that the dogs have a strong preference for the A product. It is not clear, whether the preference for A is due to its softer and more elastic structure, or if it is due simply to a better taste obtained by the enzyme treatment. It is most likely a combination of these factors, that causes the A preference.

TABLE 1

Results of Instron-measurements

| Pet food | Weight of 1st working curve - g | Weight of 5th working curve - g | Elasticity % | Initial gradient N/mm | Hardness* N/mm³ |
|---|---|---|---|---|---|
| A | 0.0465 | 0.0111 | 23.9 | 22.1 | 0.737 |
| | 0.0632 | 0.0131 | 20.7 | 25.8 | 0.862 |
| | 0.0400 | 0.0116 | 29.0 | 13.7 | 0.457 |
| | 0.0294 | 0.0100 | 34.0 | 8.71 | 0.290 |
| | 0.0282 | 0.0084 | 29.8 | 9.54 | 0.318 |
| | 0.0638 | 0.0114 | 17.9 | 34.1 | 1.14 |
| | 0.0511 | 0.0119 | 23.3 | 23.0 | 0.766 |
| | 0.0317 | 0.0082 | 25.9 | 11.0 | 0.367 |
| | 0.0496 | 0.0124 | 25.0 | 18.6 | 0.619 |
| | 0.0268 | 0.0085 | 31.7 | 8.77 | 0.292 |
| B | 0.0848 | 0.0197 | 23.2 | 38.4 | 1.28 |
| | 0.0602 | 0.0161 | 26.7 | 19.4 | 0.647 |
| | 0.1449 | 0.0096 | 6.63 | 84.8 | 2.83 |
| | 0.1310 | 0.0160 | 12.2 | 69.1 | 2.30 |
| | 0.1118 | 0.0115 | 10.3 | 93.8 | 3.13 |
| | 0.1002 | 0.0177 | 17.7 | 48.8 | 1.62 |
| | 0.1291 | 0.0039 | 3.02 | 113.1 | 3.77 |
| | 0.1040 | 0.0165 | 15.9 | 65.1 | 2.17 |
| | 0.0794 | 0.0011 | 1.39 | 160.0 | 5.33 |
| | 0.1207 | 0.0151 | 12.5 | 73.9 | 2.46 |
| Commercial Product | 0.0638 | 0.0044 | 6.90 | 11.1 | 0.369 |
| | 0.0837 | 0.0063 | 7.53 | 19.6 | 0.655 |
| | 0.0883 | 0.0092 | 10.4 | 9.48 | 0.316 |
| | 0.1093 | 0.0081 | 7.41 | 8.36 | 0.279 |
| | 0.1064 | 0.0104 | 9.77 | 10.6 | 0.352 |
| | 0.0906 | 0.0082 | 9.05 | 6.20 | 0.207 |
| | 0.0863 | 0.0046 | 5.33 | 5.16 | 0.172 |
| | 0.0739 | 0.0120 | 16.2 | 3.81 | 0.127 |
| | 0.1113 | 0.0130 | 11.7 | 9.77 | 0.326 |

*Each sample had a surface area of around 30 mm²

TABLE 2

Dry feeding Trails

| No. | Dog | Age | Weight kg | Days on trial | Daily feed of each pellets g | Total feed of each pellets for whole period g | Consump. of B for whole period g | Consump. of A for whole period g | Average pA for whole period % | Standard dev. for pA | Confidence interval for pA 95% level | Pr. for A? * | Confidence interval for pA 99% level | Pr. for A? * |
|---|---|---|---|---|---|---|---|---|---|---|---|---|---|---|
| 1 | Cocker Sp. | 9 | 10 | 14 | 250 | 3500 | 500 | 1900 | 83.7 | 27.3 | 83.7 ± 15.8 | + | 83.7 ± 33.8 | + |
| 2 | Boxer | 3 | 20 | 14 | 500 | 7000 | 1350 | 4400 | 79.6 | 12.7 | 79.6 ± 7.3 | + | 79.6 ± 10.2 | + |
| 3 | Retriever | 3 | 25 | 7 | 625 | 4375 | 800 | 2300 | 71.9 | 20.3 | 71.9 ± 18.8 | + | 71.9 ± 28.5 | − |
| 6 | Alsatian | 2 | 30 | 14 | 750 | 10500 | 3600 | 6450 | 64.2 | 20.3 | 64.2 ± 11.7 | + | 64.2 ± 16.3 | − |
| 7 | Labrador | 2 | 30 | 14 | 750 | 10500 | 2150 | 6100 | 77.1 | 29.0 | 77.1 ± 16.7 | + | 77.1 ± 23.3 | + |
| 8 | Labrador | 3 | 30 | 14 | 750 | 10500 | 2450 | 5250 | 71.6 | 29.1 | 71.6 ± 16.8 | + | 71.6 ± 23.4 | − |
| 9 | Irish setter | 2 | 20 | 14 | 500 | 7000 | 1850 | 4150 | 65.4 | 25.0 | 65.4 ± 14.4 | + | 65.4 ± 20.1 | − |
| 10 | Collie | 8 | 30 | 14 | 750 | 10500 | 6950 | 7200 | 51.5 | 13.3 | 51.5 ± 7.7 | − | 51.5 ± 10.7 | − |
| 11 | Cocker Sp. | 3 | 10 | 14 | 250 | 3500 | 2750 | 2450 | 49.1 | 24.2 | 49.1 ± 14.0 | − | 49.1 ± 19.5 | − |
| 12 | Boxer | 8 | 20 | 14 | 500 | 7000 | 850 | 5650 | 88.0 | 14.2 | 88.0 ± 8.2 | + | 88.0 ± 11.4 | + |
| 13 | Rottweiler | 2 | 30 | 14 | 750 | 10500 | 1900 | 8650 | 83.9 | 11.2 | 83.9 ± 6.5 | + | 83.9 ± 9.0 | + |
| 14 | labrador | 4 | 20 | 14 | 500 | 7000 | 2150 | 5400 | 72.5 | 13.9 | 72.5 ± 8.0 | + | 72.5 ± 11.2 | + |
| 15 | Labrador | 2 | 20 | 14 | 500 | 7000 | 6500 | 4050 | 36.7 | 13.9 | 36.7 ± 8.0 | − − | 36.7 ± 11.2 | − − |
| 16 | Cocker Sp. | 8 | 10 | 11 | 250 | 2750 | 250 | 1200 | 73.2 | 21.0 | 73.2 ± 14.1 | + | 73.2 ± 20.1 | + |
| 17 | Alsatian | 7 | 30 | 4 | 750 | 3000 | 200 | 750 | 78.4 | 15.7 | 78.3 ± 25.0 | + | 78.4 ± 45.8 | − |
| 18 | Alsatian | 5 | 30 | 4 | 750 | 3000 | 400 | 700 | 66.7 | 13.6 | 66.7 ± 21.6 | + | 66.7 ± 39.7 | − |
| 19 | Alsatian | 4 | 30 | 11 | 750 | 8250 | 750 | 3300 | 76.7 | 16.7 | 76.7 ± 11.2 | + | 76.7 ± 16.0 | + |
| 21 | Alsatian | 10 | 30 | 11 | 750 | 8250 | 2050 | 2600 | 49.7 | 35.4 | 49.7 ± 23.8 | − | 49.7 ± 33.8 | − |
| 22 | St. Bernard | 7 | 50 | 11 | 1250 | 13750 | 1600 | 6950 | 81.5 | 26.4 | 81.5 ± 17.8 | + | 81.5 ± 25.2 | + |

TABLE 2-continued

| | | | | | Dry feeding Trails | | | | | | | | |
|---|---|---|---|---|---|---|---|---|---|---|---|---|---|
| No. | Dog | Age | Weight kg | Days on trial | Daily feed of each pellets g | Total feed of each pellets for whole period g | Consump. of B for whole period g | Consump. of A for whole period g | Average pA for whole period % | Standard dev. for pA | Confidence interval for pA 95% level | Pr. for A? * | Confidence interval for pA 99% level | Pr. for A? * |
| 24 | Terrier | 7 | 30 | 7 | 750 | 5250 | 1100 | 2700 | 71.9 | 25.3 | 71.9 ± 23.4 | — | 71.9 ± 35.5 | — | preference for A
preference for neither A nor B
preference for B
Preference accepted, if 50% is not included in the confidence interval.

We claim:

1. A method for forming a pet food which consisting essentially of enzymatically hydrolyzing a proteinaceous vegetable material by an SPS-ase preparation in an aqueous medium, then formulating a pet food composition containing the enzymatically hydrolyzed proteinaceous material therein as at least 10% w/w dry substance basis of the pet food composition, and thereafter cooking and shaping said pet food composition into a pet food.

2. The method of claim 1 further comprising enzymatically hydrolyzing soy meal.

3. The method of claim 1 wherein the SPS-ase preparation is producible by cultivation of *Aspergillus aculeatus* CBS 101.43.

* * * * *

UNITED STATES PATENT AND TRADEMARK OFFICE
CERTIFICATE OF CORRECTION

PATENT NO. : 4,784,860

DATED : November 15, 1988

INVENTOR(S) : Flemming M. Christensen et al

It is certified that error appears in the above-identified patent and that said Letters Patent is hereby corrected as shown below:

Col. 1, line 65,     "texture:" should read "texture".

Col. 3, line 25,     "hours Thus" should read "hours. Thus"

Col. 7, line 40,     "batch a" should read "batch A".

Col. 8, line 6,     "minute (2)" should read "minute, (2)".

Col. 9 and 10, immediately below TABLE 2     "Trails" should read "Trials".

Col. 11 and 12, immediately below TABLE 2-cont.     "Trails" should read "Trials".

Col. 11, at the end of TABLE 2     "preference for A" should read "+preference for A".

"preference for neither A nor B" should read "-preference for neither A nor B".

"preference for B" should read "-- preference for B".

"Preference accepted if ..." should read "*Preference accepted if ...".

UNITED STATES PATENT AND TRADEMARK OFFICE
CERTIFICATE OF CORRECTION

PATENT NO. : 4,784,860

DATED : November 15, 1988

INVENTOR(S) : Flemming M. Christensen et al.

It is certified that error appears in the above-identified patent and that said Letters Patent is hereby corrected as shown below:

Col. 11, line 17, "consisting" should read -- consists --.

Signed and Sealed this

Ninth Day of May, 1989

Attest:

DONALD J. QUIGG

Attesting Officer

Commissioner of Patents and Trademarks